(12) United States Patent
Kalden et al.

(10) Patent No.: US 7,262,167 B2
(45) Date of Patent: Aug. 28, 2007

(54) DRUG, IN PARTICULAR FOR MODULATING THE IMMUNOLOGICAL RESPONSE FOR THE CONTROL OF VIRUSES, TUMORS, BACTERIA AND PARASITES

(75) Inventors: Joachim Robert Kalden, Erlangen (DE); Martin Herrmann, Neunkirchen (DE); Reinhard Voll, Eggolsheim (DE); Wolf Maximilian Bertling, Erlangen (DE); Klaus von der Mark, Hemhofer (DE); Otmar Zoller, Kempten (DE)

(73) Assignee: EXiBONA Ltd., Berkshire (GB)

( * ) Notice: Subject to any disclaimer, the term of this patent is extended or adjusted under 35 U.S.C. 154(b) by 548 days.

(21) Appl. No.: 10/639,015

(22) Filed: Aug. 11, 2003

(65) Prior Publication Data

US 2004/0096467 A1    May 20, 2004

Related U.S. Application Data

(63) Continuation-in-part of application No. 09/068,324, filed as application No. PCT/EP96/04791 on Nov. 4, 1996, now abandoned.

(30) Foreign Application Priority Data

Nov. 6, 1995    (DE) .................................. 195 41 284

(51) Int. Cl.
*A01N 1/02* (2006.01)
*A61K 38/00* (2006.01)

(52) U.S. Cl. ............................. 514/12; 530/324; 435/2
(58) Field of Classification Search .................... None
See application file for complete search history.

(56) References Cited

U.S. PATENT DOCUMENTS 5,262,406 A    11/1993    Vitale

FOREIGN PATENT DOCUMENTS

| DE | 195 41 284 | 5/1996 |
| EP | 0 505 817 A1 | 9/1992 |
| WO | WO93/06230 | 4/1993 |
| WO | WO93/11222 | 6/1993 |

OTHER PUBLICATIONS

Sestier et al C.R. Acad. Sci. Paris, Sciences de la vie/life Sciences, 1995; 318:1141-1146.*
BBA Biochimica et Biophysica Acta, "Okadaic acid increased annexin I and induced differentiation of human promyelocytic leukemia cells", Eisuke F. Sato, Keisuke Edashige, Masayasu Inoue, Kozo Utsumi, Dec. 1, 1994.
The Anatomical Record, "Lipocortin 1 in Apoptosis: Mammary Regression", James A. McKanna, Nov. 7, 1994.
The Rockefeller University Press, vol. 182, Nov. 1995, "Early Redistribution of Plasma Membrane Phosphatidylserine Is a General Feature of Apoptosis Regardless of the Initiating Stimulus: Inhibition by Overexpression of Bcl-2 and Abl", Seamus J. Martin et al.
Benet et al., pp. 3-32, in The Pharmacological Basis of Therapeutics, Eight ed., McGraw-Hill, Inc., New York, 1990.
Huang et al., FEBS Letters 392:59-62, 1996.
Lima et al., Experientia 30/8:945-946, 1974.
Neurath et al., Virology 204:475-477, 1994.
Tait et al., J. Clin. Lab. Med.:741-748, 1994.
Rabinovich et al., Science, 265:1401-1404, Sep. 1994.
Rice et al., Advances in Pharmacology, 33:389-438, 1995.
Sigma Chemical Company Catalog of Biochemicals and Organic Compounds, pp. 123 and 820-823, 1994.
Nelson et al., pp. 604-626 in Clinical Diagnosis & Laboratory Management by Laboratory Methods, Henry J.B. ed., W.B. Saunders Company, Philadelphia, 1991.
Boas et al., Proceedings of the National Academy of the Sciences 95(6):3077-3081, Mar. 17, 1998.
Bodey et al., Anticancer Research, 20(4):2665-2676, 2000.
Golden, F., p. 44 in Gorman, C., Time, May 18, 1998:37-46.
Gura, T., Science 278:1041-1042, Nov. 1997.
Jain, R.K., Cancer and Metastasis Reviews 9:253-266, 1994.

* cited by examiner

*Primary Examiner*—Sheela J. Huff
(74) *Attorney, Agent, or Firm*—Pearne & Gordon LLP

(57) ABSTRACT

A method of treating tumors and other conditions in a patient is provided. The method involves administering to the patient a treatment medicament. The medicament contains a first component and a second component. The first component can be a quantity of tumor cells derived from the patient, and the second component is a quantity of annexin, preferably annexin V. The first component and second component are provided in a therapeutically effective treatment amount. Other conditions can also be treated with annexin.

23 Claims, 1 Drawing Sheet

DRUG, IN PARTICULAR FOR MODULATING THE IMMUNOLOGICAL RESPONSE FOR THE CONTROL OF VIRUSES, TUMORS, BACTERIA AND PARASITES

CROSS REFERENCE TO RELATED APPLICATIONS

This is a continuation in part of application Ser. No. 09/068,324, filed Jan. 22, 1999, now abandoned, which is a 371 of PCT/EP96/04791 filed Nov. 4, 1996, the contents of which are incorporated herein by reference in their entirety.

FIELD OF THE INVENTION

The invention relates to a medicament, in particular for modulation of the immune response in the control of viruses, tumors, bacteria and parasites. The invention further relates to the use of an active compound for the production of a medicament.

BACKGROUND OF THE INVENTION

Phosphatidylserine-dependent Phagocytosis

Phosphatidylserine is a negatively charged phospholipid which is located in the inner layer of the plasma membrane in all cells. Occasionally, however, a phosphatidylserine molecule translocates to the outer layer of the plasma membrane. In living healthy cells, phosphatidylserine which has reached the outer layer is immediately transported back enzymatically to the inner layer of the plasma membrane. In contrast, the phosphatidylserine remains in the outer cell membrane layer in aged and in *Plasmodium falciparum*-infected erythrocytes, in sickle cells, post-inflammatory granulocytes and in apoptotic cells. If a certain degree of phosphatidylserine exposure is reached, phagocytes bind to these cells, which still maintain the integrity of their plasma membranes, via the phosphatidylserine receptor. If the phosphatidylserine density reaches a certain threshold value, the cells which are committed to die are very rapidly phagocytozed. In this process, no release of the cell contents to the surrounding tissue and therefore no activation of the immune system occurs. For this reason, this phagocytosis pathway, which depends on the recognition of phosphatidylserine on the surface of a dying cell, is called non-inflammatory.

The Role of Phosphatidylserine-dependent Phagocytosis in Malaria-infections

In the course of physiological tissue turn-over, when cells which have grown old are removed, e.g. erythrocytes and apoptotic cells, such as post-inflammatory granulocytes, a specific immunosuppression is essential, since in these cases a pro-inflammatory phagocytosis would result in autoimmune phenomena. The non-inflammatory phagocytosis of *Plasmodium falciparum*-infected erythrocytes, however, is responsible, inter alia, for the extremely poor immune response and difficulties in the immunization against malaria. No measure described to date or prophylaxis against malaria considers the circumstance in which *Plasmodium falciparum*-infected erythrocytes are taken up into phagocytes by phosphatidylserine-dependent phagocytosis. Medicaments which affect this phagocytosis pathway are presently unknown.

The Role of Phosphatidylserine-dependent Phagocytosis in Viral Infections

The role of the phosphatidylserine-dependent phagocytosis pathway is similar in viral infections. Viruses which are taken up into phagocytes through the phagocytosis of virus-infected apoptotic cells can thus escape immunosurveillance. The uptake of HIV in monocytes, for example, which takes place without triggering of the "respiratory burst", is responsible for the penetration of the HIV into the long-lived monocyte pool, which is early and unnoticed by the immune system. This infection of the monocytes/macrophages, which is presently not understood, is held causally responsible for the persistence of HIV and thus for the formation of the AIDS syndrome. Although the route of infection of monocytes/macrophages with HIV is presently still not clearly identified in molecular terms, an involvement of phosphatidylserine and the phosphatidylserine receptor is probable because of the non-inflammatory phagocytosis. It was for example possible to show, that retrovirus genomes from apoptotic cell debris can be taken up into cells and cause an infection of these cells. Since HIV can survive for a very long time in monocytes, and is possibly spontaneously released even years after the infection, the human immune system cannot completely eliminate the HIV from the body. Since the HIV damages the immune system somewhat on each release by destroying the CD 4-positive cells, the full degree of the AIDS syndrome can thus take several years to develop. Similar problems also exist in the elimination of other viruses persisting or replicating in phagocytes.

Other retroviruses and particularly the subgroup of the lentiviruses can especially be mentioned here. Some of these viruses (e.g. EIAV, Maedi Visna Virus, CAEV) persist in the phagocytes of hoofed animals and lead to autoimmune diseases. No previously described measure or prophylaxis against HIV infection or infection with other viruses surviving in phagocytes considers the circumstance in which apoptotic cells can be phagocytozed via the phosphatidylserine-dependent pathway. Medicaments which block or modify this phagocytosis pathway are presently unknown.

The Role of Phosphatidylserine-dependent Phagocytosis in Sickle Cell Anemia

The situation is different in patients with sickle cell anemia. Owing to the continuous and extremely rapid phagocytosis of autologous, genetically modified erythrocytes, anemia occurs in these patients, which can lead to death in severe cases if untreated. Here, the fact that the phosphatidylserine mediated phagocytosis proceeds in a non-inflammatory manner is less prominent than the fact that phosphatidylserine-exposing cells are eliminated in an extremely rapid and efficient way. Since there are no medicaments which block or modify this phagocytosis pathway, sickle cell anemia is presently treated with repeated blood transfusions.

The Role of Phosphatidylserine-dependent Phagocytosis in Erythrocyte Stability

A problem similar to that in sickle cell anemia also occurs in the storage of erythrocytes for transfusion. Even under blood bank conditions, an increasing number of erythrocytes exposes phosphatidylserine on their surface during storage. After the transfusion, these erythrocytes are very rapidly cleared by phagocytes and thus are lost. Moreover, the transfusion of a substantial amount of aged erythrocytes exposing phosphatidylderine on their surfaces can be stressful to the recipient's organism. Since there are presently no medicaments or additives to conserved blood which prevent this phagocytosis, the storage of erythrocytes is strictly limited in terms of time.

The Role of Phosphatidylserine-dependent Phagocytosis in Cancer Therapy

Tumor vaccines prepared of autologous apoptotic cancer cells, after injection are usually rapidly eliminated by macrophages via anti-inflammatory phagocytosis and therefore do not result in an efficient sensitization of the immune system to the tumor.

In the preparation of tumor vaccines, the tumor cells returned to the bodies of patients or experimental animals are irradiated in order to prevent the formation of metastases. Since under these circumstances apoptosis is induced in the tumor cells and these are then eliminated in a non-inflammatory manner via the phosphatidylserine-dependent phagocytosis pathway, only a relatively weak immune response usually occurs to the respective tumor. Since at present no substances are known which block or modify the phosphatidylserine-dependent phagocytosis pathway, classical immunization routes and adjuvants are currently used in order to increase the immune response to tumor cells.

Cancer vaccines pursue the strategy of a specific activation of the immune system to achieve the recognition and elimination of the tumor. One possibility is the use of whole tumor cells as vaccines since they display cancer-associated antigens as the immunological key to the destruction of the tumor they were derived from. An obstacle of these vaccinations is the weak immunogenicity of cancer cells alone, which could be overcome by the additional use of immunostimulatory or response modifying molecules. Annexin V is a monomeric protein ligand of anionic phospholipids and exhibits high affinity to membrane bound phosphatidylserine, which is translocated from the inner to the outer cell membrane layer in apoptotic cells. Apoptotic tumor cells do express phosphatidylserine and consequently might maintain an anti-inflammatory and non-immunogenic environment. Apoptotic tumor cells coated with chicken annexin V lack the phosphatidylserine signal on their surface which reduces the interaction with its receptor. In this case, phagocytosis occurs via different receptors, inducing macrophages to secrete pro-inflammatory mediators and dendritic cells to migrate and maturate, thus achieving a specific immune response against the tumor.

Immunological Background

Regulation of the cell number is a key process to normal development and hemostasis in the healthy adult. Organisms keep the correct number of cells by a genetically controlled and well-regulated process of programmed cell death called apoptosis (Kerr, J. F. R., Wyllie, A. H., Currie, A. R. 1972. Apoptosis: a basic biological phenomenon with wide ranging implications in tissue kinetics. Br. J. Cancer 26, 239-57). Typical apoptotic features of a cell are nuclear condensation, cell shrinkage (in opposite to the swollen appearance of necrotic cells), membrane blebbing and protein and DNA fragmentation.

A crucial part of apoptosis is the removal of the intact dying cell from the tissue before it causes inflammatory responses. This occurs through phagocytosis by macrophages. Phospholipids are asymmetrically distributed between the inner and outer layer of the plasma membrane with phosphatidylcholine and sphingomyelin exposed on the external layer of the membrane, and phosphatidylserine, phosphatidic acid and phosphatidylethanolamine predominantly observed on the inner surface facing the cytosol. In cells undergoing apoptosis, as well as after platelet activation or endothelial cell injury, phosphatidylserine is translocated to the outer layer of the membrane and is one of the "eat-me" ligands present on the cell surface during apoptosis (Fadok, V. A., Voelker, D. R., Campbell, P. A., Cohen, J. J., Bratton, D. L., Henson, P. M. 1992. Exposure of phosphatidylserine on the surface of apoptotic lymphocytes triggers specific recognition and removal by macrophages. J. Immunol. 148, 2207-2216). Once committed to die, the cell exposes phosphatidylserine at its surface within minutes while maintaining the integrity of the plasma membrane. Macrophages recognize phosphatidylserine via a specific receptor and thereby activate intracellular pathways which orchestrate uptake of the apoptotic cell.

Phosphatidylserine exposed at the cell surface exhibits pro-coagulant activities. Annexin V, originally discovered as an anticoagulant with an antithrombotic activity in vivo, binds with high affinity to phosphatidylserine on apoptotic cells and thereby impairs the pro-coagulant activities of the dying cell (Reutelingsperger, C. P. M. and van Heerde, W. L. 1997. Annexin V, the regulator of phosphatidylserine-catalyzed inflammation and coagulation during apoptosis. Cell. Mol. Life Sci. 53, 527-32). Fluorescently labeled annexin V is routinely used for the detection of apoptotic cells in flow cytometric assays (Van Engeland, M., Nieland, L. J. W., Ramaekers, F. C. S., Schutte, B., Reutelingsperger, C. P. M. 1998. Annexin V-affinity assay: a review on an apoptosis detection system based on phosphatidylserine exposure. Cytometry 31, 1-9).

The immune system has to contend with the consequences of two types of cell death, necrosis and apoptosis. Apoptosis, as described above, is the physiological form for the non-inflammatory removal of intact dying cells during normal tissue turn over. Unremoved apoptotic cells further proceed to the stage of secondary necrosis and are identically handled. Primary necrosis, in contrast, is a pathological event resulting in cell lysis and consequently in the induction of inflammation.

Two different types of antigen presenting cells (APC), macrophages and dendritic cells (DC), are involved in the clearance of dying cells: Macrophages degrade and process antigens contained within apoptotic cells, but they fail to induce antigen-specific cytotoxic T lymphocytes (CTL) when injected in vivo. After phagocytosis of apoptotic cells macrophages modulate the immune response by the release of immunosuppressive factors and the failure to present antigen, whereas exposure to primary necrotic cells leads to activation of macrophages towards inflammation. The response against secondary necrotic cells comprises features of the response against apoptotic cells as well as features of the response against necrotic cells.

Optimal cross-presentation of antigens acquired from dying cells by DC requires two steps: (i) phagocytosis of dying cells in the immature DC state and (ii) receipt of an appropriate maturation signal. Immature DC are located in the body's periphery, capture antigen and thus receive a signal to leave the tissue and migrate to the regional lymph node. A maturation signal can be provided e.g. by necrotic cell fragments and leads to a 5-10 fold improved antigen presentation via upregulation of MHC (major histocompatibility complex) and costimulatory molecules and the capacity to induce antigen specific $CD4^+$ and $CD8^+$ T cells. In contrast, phagocytosis of apoptotic cells in early stages of apoptosis fails to induce full maturation and may lead to the induction of tolerance to self and considerably low immunogenicity. (Sauter, B., Albert, M. L., Francisco, L., Larsson, M., Somersan, S., Bhardwaj, N. 2000. Consequences of cell death: Exposure to necrotic tumor cells, but not primary tissue cells or apoptotic cells, induces the maturation of immunostimulatory dendritic cells. J. Exp. Med. 191, 423-433).

Autologous apoptotic tumor cells are scavenged and degraded by macrophages, thereby preventing accumulation of high amounts of autoantigens in areas of cell death. Under these conditions macrophages actively suppress autoimmune responses through production of anti-inflammatory cytokines like transforming growth factor β (TGF-β), interleukin (IL)-10, platelet activating factor (PAF), and prostaglandin $E_2$ ($PGE_2$) and through inhibition of pro-inflammatory cytokines like IL-1β, tumor necrosis factor (TNF)-α, granulocyte macrophage-colony stimulating factor (GM-CSF), IL-12 and IL-8 (Voll, R. E., Hermann, M., Roth, E. A., Stach, C., Kalden, J. R. 1997. Immunosuppressive effects of apoptotic cells. Nature 390, 350-351; Fadok, V. A., Bratton, D. L., Konowal, A., Freed, P. W., Westcott, J. Y., Henson, P. M. 1998. Macrophages that have ingested apoptotic cells in vitro inhibit pro-inflammatory cytokine production through autocrine/paracrine mechanisms involving TGF-β, $PGE_2$, and PAF. J. Clin. Invest. 101, 890-898). Immature dendritic cells fail to receive an adequate full maturation signal after phagocytosis of apoptotic tumor cells. The overall result is low immunogenicity of apoptotic tumor cells. Tumors most probably undergo some level of cell turn over through the cell death mechanism of apoptosis thereby circumventing an effective immune response.

It is believed that the phosphatidylserine receptor (PSR) serves as a crucial switch that controls the development of inflammation and/or the initiation of the adaptive immune response. (Henson, P. M., Bratton, D. L., Fadok, V. A. 2001. The phosphatidylserine receptor: a crucial molecular switch? Nature Rev. Mol. Cell Bio. 2, 627-633). This theory is supported by the fact that macrophages and DC are obviously able to distinguish, whether a cell is going to die by apoptosis or necrosis.

For cases in which sufficient ligation of the PSR occurs, e.g. by an apoptotic cell which expresses phosphatidylserine externally, suppression may dominate: downregulation of pro-inflammatory cytokines through the release of TGF-β by macrophages is induced and DC-maturation inhibited.

Uptake of apoptotic and remarkably also secondary necrotic cells does not result in DC maturation and antigen presentation, but primary necrotic cells, particularly tumor cells, can activate the response. In this case, when ligation of the PSR is insufficient, the pro-inflammatory and immune-stimulatory effects take over: secretion of pro-inflammatory cytokines and maturation of DC are induced. Thus, APC are able to distinguish two types of cell death, with primary necrosis providing a critical signal that will promote the initiation of immunity.

There are two possible mechanisms to overcome the dominant anti-inflammatory effect of PSR ligation. The susceptibility of the PSR to protease cleavage leads to the assumption that proteases e.g. released by primary necrotic cells would remove the PSR receptor from the cell surface resulting in transiently unprotected cells that could be triggered to produce pro-inflammatory mediators and/or to fully mature towards an antigen-presenting and immune response stimulating dendritic cell (Fadok, V. A., Bratton, D. L., Guthrie, L. A., Henson, P. M. 2001. Differential effects of apoptotic vs. lysed cells on macrophage production of cytokines: role of proteases. J. Immunol. 166, 6847-6854).

Another possible mechanism is the assumption that proteins known to bind phosphatidylserine with high affinity, such as annexins, will be able to block the exposed phosphatidylserine to reduce its interaction with the PSR. Annexin V coating the surface of an apoptotic cell and thereby shielding the PSR most probably reduces the interaction of phosphatidylserine with its receptor. Several other cell surface or bridging molecules interacting with phosphatidylserine might also be impaired. The overall result would be the loss of the dominating PSR function, the stimulation of macrophages to create a pro-inflammatory environment and a signal for the full maturation of dendritic cells, their migration to lymph nodes, and immune stimulatory antigen presentation, resulting in the stimulation of a specific T cell response.

According to the prior art, annexins are additionally known. Annexin V is a member of a ubiquitously occuring family of annexin proteins which share structural and functional features (Mollenhauer, J. 1997. Multi-author review. Annexins: what are they good for? Cell Mol. Life Sci. 53, 506-556). The common property of annexins is the reversible calcium-dependent binding to anionic phospholipid membranes. Although this property may be due to highly conserved sequences, the existence of at least 13 different annexins in mammalian species suggests that they have specific and diverse biological functions. These functions relate to membrane associated processes, and recent data show their function in the regulation of thrombosis, hemostasis and apoptosis.

Specificity and diversity of annexins may be provided by their N-terminal domains (which are less conserved among different members of the annexin family), but may also be the consequence of interactions of annexins either with other members of this protein family or other cellular partners. Typically, annexins have molecular weights ranging between 30 and 40 kD (only annexin VI is exceptional with regard to its molecular weight of 66 kD).

The annexins also participate in intracellular membrane trafficking during exo- and endocytosis, phagosome formation, and lipid raft clustering (reviewed in Reutelingsperger, C. P. M. 2001. Annexins: key regulators of haemostasis, thrombosis, and apoptosis Thromb. Haemost. 86, 413-419). They inhibit cytosolic phospholipases and protein kinases. Annexin V also possesses a voltage-dependent $Ca^{2+}$ ion channel activity (Voges, D., Berendes, R., Demange, P. et al. 1995. Structure and function of the ion channel model system annexin V. Adv. Enzymol. Relat. Areas Mol. Biol. 71, 209-239). This kind of activity needs penetration of annexin V into the hydrophobic core of the lipid bilayer, which was recently shown under mild acidic conditions (pH 5-6) (Isas, J. M., Cartailler, J. P., Sokolow, Y., Patel, D. R., Langen, R., Luecke, H., Hall, J. E., Haigler, H. T. 2000. Annexins V and XII insert into bilayers at middly acidic pH and form ion channels. Biochemistry 39, 3015-22).

While many annexin functions are intracellular, others occur outside the cell. Annexin V was found in extracellular fluids like cerebrospinal fluid and blood plasma. The pathway of its externalisation is not fully understood. Once present in the extracellular space, the annexins have been shown to function as receptors for many polypeptide ligands and exhibit a variety of extracellular activities: annexin V binds with high affinity to phospholipid membranes of platelets, inhibits lipid-dependent reactions of the blood coagulation and intravascular thrombus formation, binds to collagens and exhibits lectin activity, i.e. binds to carbohydrate moieties of glycoproteins (Seaton, B. A., Dedman, J. R. 1998. Annexins. Bio. Metals 11, 399-404; Turnay, J., Pfannmüller, E., Lizarbe, M. A., Bertling, W., von der Mark, K. 1995. Collagen binding activity of recombinant and N-terminally modified annexin V (anchorinCII) J. Cell.

Biochem. 58, 208-220; Mollenhauer, J. 1997. Multi-author review. Annexins: what are they good for? Cell Mol. Life Sci. 53, 506-556).

Recently, a new class of diseases called the "annexinopathies" was postulated, characterized by an aberrant expression of annexin II or V (Rand, J. H. 1999. "Annexinopathies"—A new class of diseases. N. Engl. J. Med. 340, 1035-36). These diseases strongly indicate that these annexins exhibit a role in the physiological control of blood coagulation.

The medicaments and procedures known according to the prior art, in particular the adjuvants employed today, stimulate the immune system non-specifically. To date, no agent is yet described which prevents or modifies the phagocytosis of phosphatidylserine-exposing cells, thus leading to a specific immunostimulation. The disadvantages which occur in non-inflammatory clearing of whole cell vaccines and virus-infected cells are particularly to be emphasized. On the one hand, phosphatidylserine-dependent phagocytosis contributes to the ineffectivity of vaccines through their breakdown, on the other hand to virus persistence.

Since, in sickle cell anemia, even young erythrocytes expose phosphatidylserine on their surface, they are removed by the endogenous phagocytes. This contributes disadvantageously to the anemia of the patients.

Even for the storage of blood and erythrocytes, no medicaments or additives are known which prevent the breakdown of the donor erythrocytes by the recipient's phagocytes after transfusion. This presently leads to a relatively short shelf life of conserved blood and erythrocyte concentrates and to a marked loss of activity in preserves stored for a long time period.

The object of the present invention is to eliminate the disadvantages according to the prior art. In particular, a medicament or the use of an active compound which brings about an increase in the immunity to viruses, tumors, bacteria and parasites will be specified.

SUMMARY OF THE INVENTION

A method of treating tumors in a patient such as a human being is provided. The method involves administering to the patient a treatment medicament. The medicament contains a first component and a second component. The first component is a quantity of tumor cells derived from the patient, and the second component is a quantity of annexin. The first component and second component, in combination, are provided in a therapeutically effective treatment amount. Methods of treating sickle cell anemia, removing phosphatidylserine-exposing erythrocytes from whole blood or another erythrocyte-containing preparation, and extending the storage life of whole blood and erythrocyte concentrations, are also provided.

DETAILED DESCRIPTION OF THE PREFERRED EMBODIMENTS OF THE INVENTION

Figure 1:
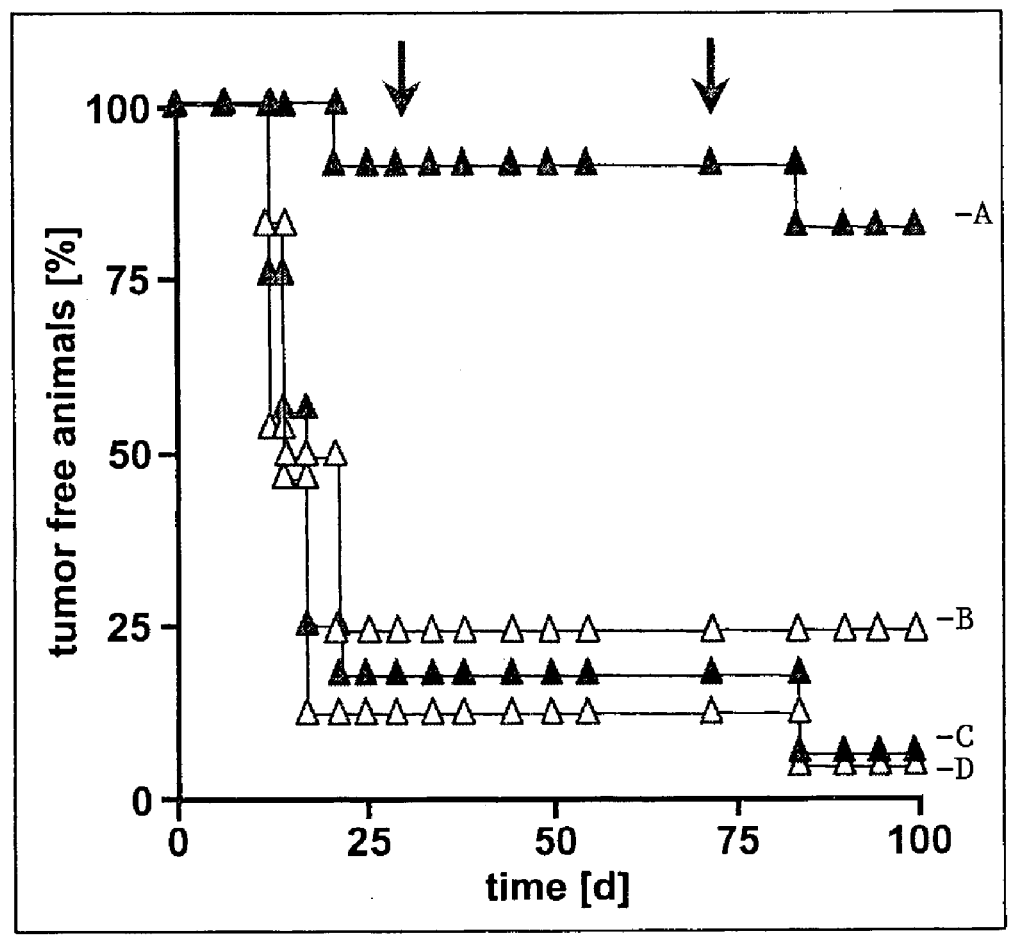
FIG. 1 is a graph illustrating protection of mice from lethal challenge after vaccination with apoptotic lymphoma cells in combination with annexin V. A=apoRMA+AxV; B=apoRMA; C=PBS+AxV; D=PBS.

If a preferred range such as 5-25 is set forth herein, this means preferably at least 5 and, separately and independently, preferably not more than 25. If a listing of alternative quantities is given, it is understood that this also includes ranges between any of the numbers listed. According to the invention, an active compound selected from the following group is contained in a medicament for influencing the phosphatidylserine-dependent phagocytosis, in particular for modulation of the immune response in the control of viruses, tumors, bacteria and parasites: annexin, fragments of annexin, modified annexin, annexin antibodies, annexin ligands, phosphatidylserine or phosphodiesterase.

According to the invention, the use of an active compound for the production of a medicament, in particular for modulation of the immune response in the control of viruses, tumors, bacteria and parasites, is additionally provided, the active compound for influencing the phosphatidylserine-dependent phagocytosis being selected from the following group: annexin, fragments of annexin, modified annexin, annexin antibodies, annexin ligands, phosphatidylserine or phosphodiesterase.

The present invention includes a method and composition for treating tumors. The method comprises administering to a patient, such as a human, suffering from a tumor a treatment medicament comprising, in combination, an amount of a first component and an amount of a second component, said first component being tumor cells withdrawn from the patient, said second component being a quantity of annexin, preferably annexin V, the amount of the first component and the amount of the second component, in combination, being a therapeutically effective treatment amount. The first and second components, in combination, are preferably administered by intradermal injection, and in such an administration method are preferably suspended or dissolved together in a pharmaceutically acceptable carrier.

The withdrawn tumor cells may be treated with annexin or annexin V ex corpore and returned to the patient as detailed above.

As used herein and in the claims, each of the terms annexin and annexin V is defined to include its pharmaceutically acceptable derivations. The annexin and annexin V utilized herein is preferably carried in a pharmaceutically acceptable carrier as mentioned herein or as otherwise known in the art.

"Therapeutically effective amount" and "therapeutically effective treatment amount" generally includes the dosages set forth herein. A person skilled in the art will be aware that the optimum dosage range has to be determined separately for each kind of tumor. The medicament is preferably administered by intradermal injection, but also intravenous, intramuscular, subcutaneous, or intratumoral injection.

Dosages for children are generally less than dosages for adults.

The dose of annexin V for anti-tumor vaccination is related to the amount of tumor-cell protein, which is beforehand determined as an equivalent to a certain tumor-cell number. The annexin V doses are preferably the following:

| mg annexin V | mg tumor protein |
| --- | --- |
| 0.01 | 0.24 |
| 0.02 | 0.48 |
| 0.05 | 1.20 |
| 0.10 | 2.40 |
| 0.20 | 4.80 |
| 0.30 | 7.20 |
| 0.40 | 9.60 |
| 0.50 | 12.00 |

-continued

| mg annexin V | mg tumor protein |
|---|---|
| 0.70 | 16.80 |
| 0.80 | 19.20 |
| 0.90 | 21.60 |
| 1.00 | 24.00 |
| 2.00 | 48.00 |
| 3.00 | 72.00 |
| 5.00 | 120.00 |
| 10.00 | 240.00 |

To produce vaccination material, annexin is combined with tumor cells as measured by tumor cell protein, wherein preferably 0.01-1000 mg tumor cell protein is combined with 0.001-100 mg annexin. As used herein, 24 mg tumor cell protein corresponds to about $10^8$ tumor cell equivalents. Preferably 0.005-1000, more preferably 0.008-500, more preferably 0.01-100, more preferably 0.1-10, more preferably 0.2-5, more preferably 0.3-3, more preferably 0.5-2, more preferably about 1 mg annexin is combined with each 24 mg tumor cell protein (corresponding to about $10^8$ tumor cell equivalents) to produce vaccination or treated material. The annexin is preferably annexin V, preferably chicken annexin V. A single vaccination dosage of vaccination material preferably contains 0.01-6000, more preferably 0.1-600, more preferably 0.2-300, more preferably 0.24-240, more preferably about 24 mg tumor cell protein in combination with annexin as described above. Three vaccinations, on days 0, 21 and 42, are preferably given, but fewer or more vaccinations (such as 1, 2, 4, 5, 6, 7, etc.) can be given, such as on days 1, 2, 3, 4, 5, 6, 7, 10, 14, 18, 28, 35, 49, 56, 63, 70, etc.

Chicken annexin V is produced as a recombinant protein in *Escherichia coli*. Recombinant chicken annexin V, liquid in phosphate buffered saline (8000 mg/L NaCl, 200 mg/L KCl, 1150 mg/L $Na_2HPO_4$, 200 mg/L $KH_2PO_4$), has a concentration of 0.1-50, 1-20, 2-10 or 4.0-6.0 mg annexin V per mL. Preferably the concentration is 5 mg annexin V per mL. The solution does not require any other excipients. Any other pharmaceutically acceptable carrier can also be used. Annexin and annexin V can be used for any of the uses mentioned herein at the concentrations and/or in the solutions mentioned above.

Preparation of Tumor Cell Vaccines

The exemplary procedure described here is a treatment of renal cell carcinoma. The tumor tissue is obtained during routine surgery for the resection of a patient's tumor. Each patient-specific tumor tissue is bottled immediately after removal under sterile conditions in the operating unit into appropriately labelled containers which are pre-filled with certified suspension medium, and transported on ice to a GMP-facility. The tumor cell mass is mechanically minced into a cell suspension and passed through a sterile metal sieve. The protein content of the tumor cells is determined by the Uptima BC Assay (Interchim, Montlugon, France) according to the manufacturer's instructions. The amount of protein is calculated as an equivalent to a certain tumor-cell number. The tumor-derived cells are γ-irradiated with 100 Gy for inactivation and induction of apoptosis. Cells are harvested by centrifugation and resuspended in Ringer solution (8.6 g/L NaCl, 0.3 g/L KCl, 0.33 g/L $CaCl_2 \times 2H_2O$) supplemented with DMSO as a cryopreservative to a final concentration of 7% (v/v). Aliquots of 1.0 mL of this tumor-cell suspension for vaccination are cryoconserved and stored in sealed 1.8 mL cryo tubes in the vapor-phase of liquid nitrogen. Directly before administration to the patient, the tumor-derived cells are thawed, mixed with annexin V and incubated for 20 minutes at room temperature, thus allowing binding of annexin V to the tumor-derived cells.

Alternatively, the tumor-derived cells can be cryoconserved directly after the preparation of the cell suspensions, then thawed, γ-irradiated, coated with annexin V and administered to the patient.

Vaccination

The dose of annexin V depends on the available tumor cell number per patient received after surgery. Preferred dosages for the treatment of renal cell carcinoma and other tumors, which is described here as an example and not limiting the scope of the invention, are in the range of 0.1 mg annexin V with 2.4 mg tumor protein (corresponding to approximately $10^7$ tumor cell equivalents) to 1 mg annexin V with 24 mg tumor protein (corresponding to approximately $10^8$ tumor cell equivalents) for each vaccination. Three vaccinations with the autologous, tumor-derived irradiated and annexin V coated cells on days 0, 21 and 42 are applied intradermally near a lymph node by injection in the upper leg, approximately 10 cm below the inguinal ligament, and/or the forearm. Up to 6 injections are performed with 27G needles and contain 200 µl each and a total volume of about 1.2 mL. Alternatively, the total volume can be 0.5-5 mL. After injection the needles must be left in the skin for 20 seconds.

By means of annexin, preferably by means of annexin V, the phosphatidylserine-dependent phagocytosis can be modified or inhibited. Additionally, for example, by removal or a blockade of annexins, in particular of annexin V, the phagocytosis can be modulated or stimulated.

Particular importance is to be ascribed to use in the human or veterinary medicine field, where, in many established forms of therapy, but also in experimental forms of therapy, immunomodulation is desirable. Thus in the treatment of oncoses and of virus infections, immunostimulation is often desirable, whereas in disorders of the rheumatic type and in autoimmune disorders immunosuppression is more desirable.

An important field of use for the blockade of noninflammatory phosphatidylserine-dependent phagocytosis follows from the specific "adjuvant action" resulting therefrom. Phosphatidylserine-exposing cells are phagocytozed by a pro-inflammatory immunostimulatory alternative pathway after the blockade of the non-inflammatory phosphatidylserine-dependent phagocytosis, which is accompanied by a massively increased immune response. For this "adjuvant action", all kinds of areas of use result, e.g., in human medicine. On the one hand, the immunogenicity of tumor vaccines can be increased thereby, if these consist of irradiated and thus apoptotic tumor cells.

It is furthermore possible to achieve an immune response to those tumor cells which are radioactively irradiated in situ for therapeutic reasons. In this case, a tumor-specific immune response would increase the therapeutic success by the elimination of the residual tumor mass. In parallel with a cytostatic therapy with apoptosis-inducing agents, such as, for example, cisplatin and hydroxyurea, a similar effect can also lead to a massive tumor-specific immunostimulation. In the treatment of virus infections as well, e.g. of those viruses which persist in phagocytes, the blocking of the phosphatidylserine-dependent phagocytosis pathway leads to a specific immunostimulation. The treatment of infections with lentiviruses and HIV must be regarded as a particularly important example in this connection. Penetration of the viruses caused by phosphatidylserine-dependent phagocytosis "unnoticed" by the cell leads to death after a longer or shorter latency period in by far the most people infected. Annexins, preferably annexin V, are suitable for the treatment of HIV-infected people, since apoptotic material taken up into phagocytes by the pro-inflammatory pathway triggers a "respiratory burst" and thus leads to the destruction of the virus genomes.

Furthermore, owing to the blocking of the phosphatidylserine-dependent phagocytosis, undesirable cell losses can be avoided in vivo and in vitro. This is of great importance both in the storage of erythrocyte-containing conserved blood and as a medicament for patients with sickle cell anemia.

The use of the invention is illustrated by the following examples.

EXAMPLE 1

Use of Annexins, Preferably Annexin V, as Adjuvants for Tumor Vaccines

For the production of tumor vaccines from a patient-derived tumor, the cells are radioactively irradiated before reinjection into the patient in order to prevent formation of metastases. During the apoptosis induced thereby, phosphatidylserine is exposed on the surface of the tumor cells, which leads to only a weak immunogenicity of the tumor vaccine.

Directly before the injection, the irradiated tumor cells are incubated ex corpore with annexins, preferably annexin V, at the ratios mentioned above, in order to block or modify the phosphatidylserine-dependent phagocytosis in the patient. Additionally, an annexin, preferably annexin V, bolus (preferably 0.1-5 mL of the preferred annexin preparation mentioned above (5 mg annexin per mL)) is placed in the injection site in order to further increase the action locally.

EXAMPLE 2

Use of Annexins, Preferably Annexin V, as an Immunostimulant in Chemo- and Radiation Therapy Therapeutic radioactive irradiation and also treatment with cytostatics, induce apoptosis in corpore in cells of a variety of different tumor types. In order to prevent a non-inflammatory clearance of the dead cells and to overcome the weak immune response associated therewith, annexins, preferably annexin V, are injected into the tumor in the concentrations mentioned above after radiation therapy or chemotherapy and after an appropriate time period for the induction of apoptosis. The clearance of the dead tumor cells thereby takes place via a pro-inflammatory phagocytosis pathway and thus leads to an increased immune response to the residual tumor.

EXAMPLE 3

Storage of Whole Blood and Erythrocyte Preparations

Annexins, preferably annexih V, are added in the concentrations mentioned above to whole blood or erythrocyte concentrates in order to slow the breakdown of the phosphatidylserine-exposing erythrocytes after the transfusion and thus to increase the efficiency of the transfusion. The annexins, preferably annexin V, can in this case be added either directly after taking blood or alternatively just prior to transfusion. Erythrocyte concentrates are provided at concentration levels as known in the art; erythrocyte concentrate is produced by centrifuging whole blood and discarding the plasma, as known in the art.

Annexin, preferably annexin V, is added to whole blood at a concentration of 0.01 mg to 100 mg annexin per 100 mL whole blood, more preferably 0.1 mg to 10 mg annexin per 100 mL whole blood. Annexin, preferably annexin V, is added to erythrocyte concentrate at a concentration of 0.01 mg to 100 mg annexin per 100 mL erythrocyte concentrate, more preferably 0.1 mg to 10 mg annexin per 100 mL erythrocyte concentrate.

Alternatively, phosphatidylserine-exposing erythrocytes can be removed from whole blood or other erythrocyte-containing preparations by passing the material through, or contacting the material with, a substrate or filter or filter matrix or filter medium or similar removal structure carrying immobilized annexin, preferably annexin V. The filtration or removal can be performed immediately before transfusion or during transfusion or at any time during storage. The substrate or filter medium or removal structure can be provided by immobilizing sufficient annexin, preferably annexin V, on activated matrices according to standard procedures known in the art or on similar structures or substrates known in the art. Sepharoses, like Sepharose 4FF or Sepharose 6FF, which have been extensively applied in medical products for years, can be used as a substrate or solid support. However, other physiologically compatible materials like biopolymers or porous glass beads or other materials known in the art can be applied as well to provide the substrate or filter or filter medium or filter matrices or removal structure.

EXAMPLE 4

Use of Annexins, Preferably Annexin V, in Patients with Sickle Cell Anemia

EXAMPLE 4a

Classical Solution with Annexin, Preferably Annexin V, Infusions

In order to prevent the phagocytosis of the sickle cells, which in this syndrome contributes decisively to the anemia, annexins, preferably an annexin V solution, are administered intravenously in the concentrations and carriers mentioned above and as known in the art to very severely anemic patients. Preferably the dosage is 1 to 10000 mg, more preferably 10 to 1000 mg, more preferably 50 to 200 mg, annexin per 100 kg mass of patient per day. Preferably the treatment is a permanent treatment, preferably for as long as the patient is alive. The annexin may be administered once a day, less preferably every 2, 3, 4, 5, 6, 7, 14 or 28 days.

Example 4b

Use of Annexins, Preferably Annexin V, in the Transient Gene Therapy Approach with Vectors Derived from RNA Viruses In this approach, a fusion protein from annexins, preferably from annexin V, with a leader peptide is expressed in blood cells, e.g., monocytes, with the aid of a transient RNA vector system (e.g. a system derived from the poliovirus). In this manner, this transient in situ production as an infusion blocks the phagocytosis of the sickle cells over a relatively long period of time. Since RNA-dependent expression systems neither integrate into the genomic DNA of the host cells nor spread vertically, the expression of the annexins is only transient, which minimizes the risks of the triggering of an autoimmune pathology.

In the treatment of infections with viruses as well, e.g. of those which persist in phagocytes, the blocking of the phosphatidylserine-dependent phagocytosis pathway leads to a specific immunostimulation. The treatment of infections with lentiviruses and HIV must be regarded as a particularly important example in this connection. A penetration of the viruses "unnoticed" by the cell leads to the virus persistence in the long-lived monocyte/macrophage pool and to death in by far most of the infected people after a longer or shorter latency period. Annexins, preferably annexin V, are suitable for the treatment of HIV as described above, since apoptotic material phagocytozed via the pro-inflammatory pathway triggers a "respiratory burst" in the phagocytes and thus leads to the destruction of the virus genome.

By means of annexin, preferably annexin V, the phosphatidylserine-dependent phagocytosis can be modulated or inhibited. This may result in a immunostimulation and an increased immune response. Particular importance is to be ascribed to use in the human or veterinary medicine field, where, in many established forms of therapy, bur also in experimental forms of therapy, immunomodulation is desirable. Thus in the treatment of oncoses and virus infections, immunostimulation is often desirable, whereas in disorders of the rheumatic type and in autoimmune disorders immunosuppression is more desirable.

Phosphatidylserine-bearing cells are phagocytosed by means of an inflammatory immunostimulatory alternative pathway after the blockade of the noninflammatory phosphatidylserine-dependent engulfment phagocytosis pathway, which is accompanied by a massively increased immune response. An increase in immune response is in particular useful to treat disorders caused by bacteria, e.g. sepsis, diseases caused by bacteria and the like. For treatment of such disorders a medicament is disclosed containing a therapeutically effective amount of annexin, in particular annexin V.

EXAMPLE 5

Prophylactic Tumor Vaccination

This Example is illustrated in FIG. 1. Mice were subdermally immunized twice (day 0 and day 15) with $5 \times 10^6$ (optimized dose) UV-C-irradiated apoptotic RMA cells (apoRMA) (murine T cell lymphoma line). Prior to vaccination, these cells were incubated with or without annexin V. Control animals received phosphate buffered saline (PBS) with or without annexin V. On day 30 all animals received a lethal tumor challenge of $2.5 \times 10^4$ vital RMA cells. On day 72 protected animals received a re-challenge of $2.5 \times 10^4$ vital RMA cells.

Results:

In the vaccination group with apoRMA cells+annexin V in a dose-optimized setup, 91% of animals were protected against the first lethal tumor challenge (arrow day 30), of which 90% rejected the second challenge (arrow day 72).

Vaccination with apoRMA cells without annexin V protected only 25% of animals. In PBS-treated control animals with annexin V or without, protection was only 18% or 12%, respectively.

EXAMPLE 6

Therapeutic Tumor Vaccination

Procedure:

Mice were inoculated with a lethal tumor challenge of $2 \times 10^4$ vital RMA cells (day 0). On day 4, they were immunized with $5 \times 10^6$ (optimized dose) UV-C-irradiated apoptotic RMA cells. Prior to injection, these cells were incubated with or without annexin V.

Results:

In the vaccination group with apoRMA with annexin V in a dose-optimized setup, 60% of the animals with a tumor were cured. 10% of the animals of this group did not develop a tumor at all.

90% of the animals immunized with apoRMA without annexin developed a tumor.

EXAMPLE 7

Mode of Action of Annexin V In Vitro

Procedure:

UV-C-irradiated apoptotic RMA cells (apoRMA) were incubated with (+annexin V) or without annexin V (medium) and added to phagocytes: (i) peritoneal macrophages or (ii) bone marrow derived dendritic cells with an apoRMA:phagocyte ratio of 5:1. After 24 h the supernatants of the cell incubations were retrieved and assayed for the release of tumor necrosis factor (TNF)-α, interleukin (IL)-1β, IL-10 and transforming growth factor (TGF)-β by enzyme linked immuno sorbent assay (ELISA). Controls included untreated phagocytes (medium) or phagocytes treated with apoRMA (medium, +apoRMA) or annexin V (+annexin V) only.

Results:

Macrophages clearing apoptotic tumor cells in the presence of annexin V secreted significantly higher amounts of the pro-inflammatory cytokines IL-1β and TNF-α and a significantly lower amount of the anti-inflammatory cytokine TGF-β. IL-10 secretion was unaffected. The release of these cytokines by dendritic cells was unaffected by annexin V.

| Cytokine (pg/mL) | Macrophages | | | | Dendritic Cells | | | |
|---|---|---|---|---|---|---|---|---|
| | medium | | + annexin V | | medium | | + annexin V | |
| | / | + apoRMA | / | + apoRMA | / | + apoRMA | / | + apoRMA |
| TNF-α | 125 ± 15 | 335 ± 30 | 117 ± 24 | 978 ± 48 | 267 ± 137 | 392 ± 79 | 245 ± 121 | 426 ± 78 |
| IL-1β | 21 ± 5 | 44 ± 7 | 14 ± 1 | 322 ± 85 | 10 ± 4 | 46 ± 4 | 8 ± 3 | 47 ± 3 |
| IL-10 | 88 ± 18 | 105 ± 30 | 129 ± 11 | 90 ± 8 | 42 ± 1 | 51 ± 8 | 42 ± 2 | 43 ± 4 |
| TGF-β | 82 ± 10 | 505 ± 54 | 105 ± 11 | 193 ± 26 | 230 ± 72 | 266 ± 76 | 238 ± 93 | 261 ± 65 |

EXAMPLE 8

Mode of Action of Annexin V In Vivo

Procedure:

Three C57BL/6 mice were subcutaneously (s.c.) immunised 3-times with $5 \times 10^6$ γ-irradiated (100 Gy), OVA-transfected EG7-cells±100 µg annexin V in 3-week intervals for analysing $OVA_{257-264}$-specific CD8 T cell frequencies. To measure appropriate CD8 T cell subpopulations 5 days after the last vaccination $10^7$ murine splenocytes were re-stimulated in vitro with 1 µg/mL $OVA_{257-264}$ peptide for 3 days. Subsequently, IFN-γ-specific ELISPOT assays were performed by using $10^5$ cells of the parental EL-4, $OVA_{257-264}$-pulsed EL-4 (1 µg/mL $OVA_{257-264}$-peptide loaded onto appropriate numbers of EL-4 cells for 1 h at 37° C. in a $CO_2$-incubator) and EG7 cell line, respectively, as antigen-presenting cells and respective $10^5$ immune splenocytes as effector cells for assessing appropriate CD8 T cell numbers.

Results:

The comparison between epitope-specific CD8 T cell numbers elicited by immunisation of mice with (i) annexin V-pulsed apoptotic/secondary necrotic EG7 or (ii) apoptotic/secondary necrotic EG7 cells without annexin V-treatment clearly shows that $OVA_{257-264}$ CD8 T cell frequency is approximately 3-fold augmented in case of annexin V-mediated priming of the immune system.

What is claimed is:

1. A method of treating a tumor in a patient, comprising administering to the patient a treatment medicament comprising, in combination, an amount of a first component and an amount of a second component, said first component being a quantity of tumor cells withdrawn from the patient, said second component being a quantity of annexin, the amount of the first component and the amount of the second component, in combination, being a therapeutically effective treatment amount.

2. The method of claim 1, wherein said annexin is annexin V.

3. The method of claim 1, wherein said first and second components are administered simultaneously.

4. The method of claim 1, wherein said treatment medicament is administered by intradermal injection.

5. The method of claim 1, wherein said treatment medicament is administered by intravenous injection.

6. The method of claim 1, wherein said treatment medicament is administered by intramuscular injection.

7. The method of claim 1, wherein said treatment medicament is administered by subcutaneous injection.

8. The method of claim 1, wherein said treatment medicament is administered by intratumoral injection.

9. The method of claim 1, wherein said first component and said second component are mixed prior to administration of the medicament to the patient.

10. The method of claim 1, said medicament further comprising a pharmaceutically acceptable carrier.

11. The method of claim 10, said carrier being phosphate buffered saline.

12. The method of claim 1, wherein the ratio of the first component to the second component is (a) the quantity of tumor cells indicated by 0.01-1000 mg tumor cell protein to (b) 0.001-100 mg annexin.

13. The method of claim 1, wherein the ratio of the first component to the second component is (a) the quantity of tumor cells indicated by approximately 2.4 mg tumor cell protein to (b) 100 µg annexin.

14. The method of claim 1, wherein the ratio of the first component to the second component is (a) the quantity of tumor cells indicated by approximately 24 mg tumor cell protein to (b) 1000 µg annexin.

15. The method of claim 1, wherein the treatment medicament is administered once every 7 days.

16. The method of claim 1, wherein the volume of the treatment medicament administered to the patient is about 1.2 mL.

17. The method of claim 2, wherein the annexin V is a constituent of a fusion protein.

18. A method of treating sickle cell anemia in a patient comprising administering to said patient a therapeutically effective amount of annexin.

19. The method of claim 18, wherein said annexin is annexin V.

20. A method of treating a tumor in corpore in a patient comprising the steps of treating said tumor in corpore with radiation therapy or chemotherapy and thereafter treating said tumor in corpore with a therapeutically effective amount of annexin.

21. The method of claim 20, wherein said annexin is annexin V.

22. A method of extending the storage life of whole blood or an erythrocyte concentrate comprising the steps of providing a quantity of whole blood or erythrocyte concentrate and combining said quantity with an amount of annexin effective to extend the storage life of said quantity or increase the efficiency of a subsequent transfusion.

23. The method of claim 22, wherein said annexin is annexin V.

* * * * *